| United States Patent [19] | | [11] Patent Number: | 4,939,244 |
|---|---|---|---|
| Lee | | [45] Date of Patent: | Jul. 3, 1990 |

[54] PSEUDOAGLYCONES OF LL-E33288 ANTIBIOTICS

[75] Inventor: May D. Lee, Monsey, N.Y.

[73] Assignee: American Cyanamid Company, Stamford, Conn.

[21] Appl. No.: 4,153

[22] Filed: Jan. 30, 1987

[51] Int. Cl.$^5$ .................... C07H 15/00; C07H 1/00
[52] U.S. Cl. .................... 536/17.6; 536/16.8; 536/17.5; 536/18.6; 536/18.4; 536/54; 536/122; 536/124
[58] Field of Search .............. 424/117, 124; 536/16.8, 536/16.9, 18.5, 18.6, 122, 124, 127, 54, 17.5, 17.6, 18.4

[56] References Cited

U.S. PATENT DOCUMENTS

| 3,011,947 | 12/1961 | Preud'homme et al. | 424/124 |
|---|---|---|---|
| 3,014,841 | 12/1961 | Smith et al. | 424/124 |
| 3,206,360 | 9/1965 | Jahnke et al. | 424/124 |
| 3,221,008 | 11/1965 | Wolf et al. | 424/124 |
| 3,565,885 | 2/1971 | Molotsky et al. | 536/18.6 |
| 3,759,896 | 9/1973 | Komatsu et al. | 536/127 |
| 3,951,746 | 4/1976 | Weinstein et al. | 536/16.8 |
| 4,322,343 | 3/1982 | DeBono | 424/118 |
| 4,322,406 | 3/1982 | DeBono et al. | 424/118 |
| 4,530,835 | 7/1985 | Bunge et al. | 424/117 |
| 4,539,203 | 9/1985 | Brankiewicz et al. | 424/117 |
| 4,554,162 | 11/1985 | Young et al. | 424/117 |
| 4,563,442 | 1/1986 | Clem et al. | 424/118 |
| 4,594,248 | 6/1986 | Wilton et al. | 424/117 |
| 4,675,187 | 6/1987 | Konishi et al. | 424/117 |
| 4,694,069 | 9/1987 | Dingerdissen et al. | 424/118 |
| 4,699,790 | 10/1987 | Kirby et al. | 424/117 |
| 4,742,045 | 5/1988 | Verma et al. | 514/9 |

FOREIGN PATENT DOCUMENTS

| 0132082 | 1/1985 | European Pat. Off. | 424/117 |
|---|---|---|---|
| 45-2078 | 1/1970 | Japan | 424/124 |

OTHER PUBLICATIONS

Bunge et al.; J. of Antibiotics 37(12):1566–1571 (12–1984).
Lee et al.; Chemical Abstracts 105:77578p (1986).

Primary Examiner—Ronald W. Griffin
Assistant Examiner—Nancy S. Carson
Attorney, Agent, or Firm—H. G. Jackson

[57] ABSTRACT

Degradation products, termed pseudaglycones, of LL-E33288, BBM-1675, FR-900405, FR-900406, PD 114759, PD 115028, CL-1577A, CL-1577B, CL-1577D, CL-1577E and CL-1724 antibiotics/antitumor agents are disclosed anad described.

4 Claims, 11 Drawing Sheets

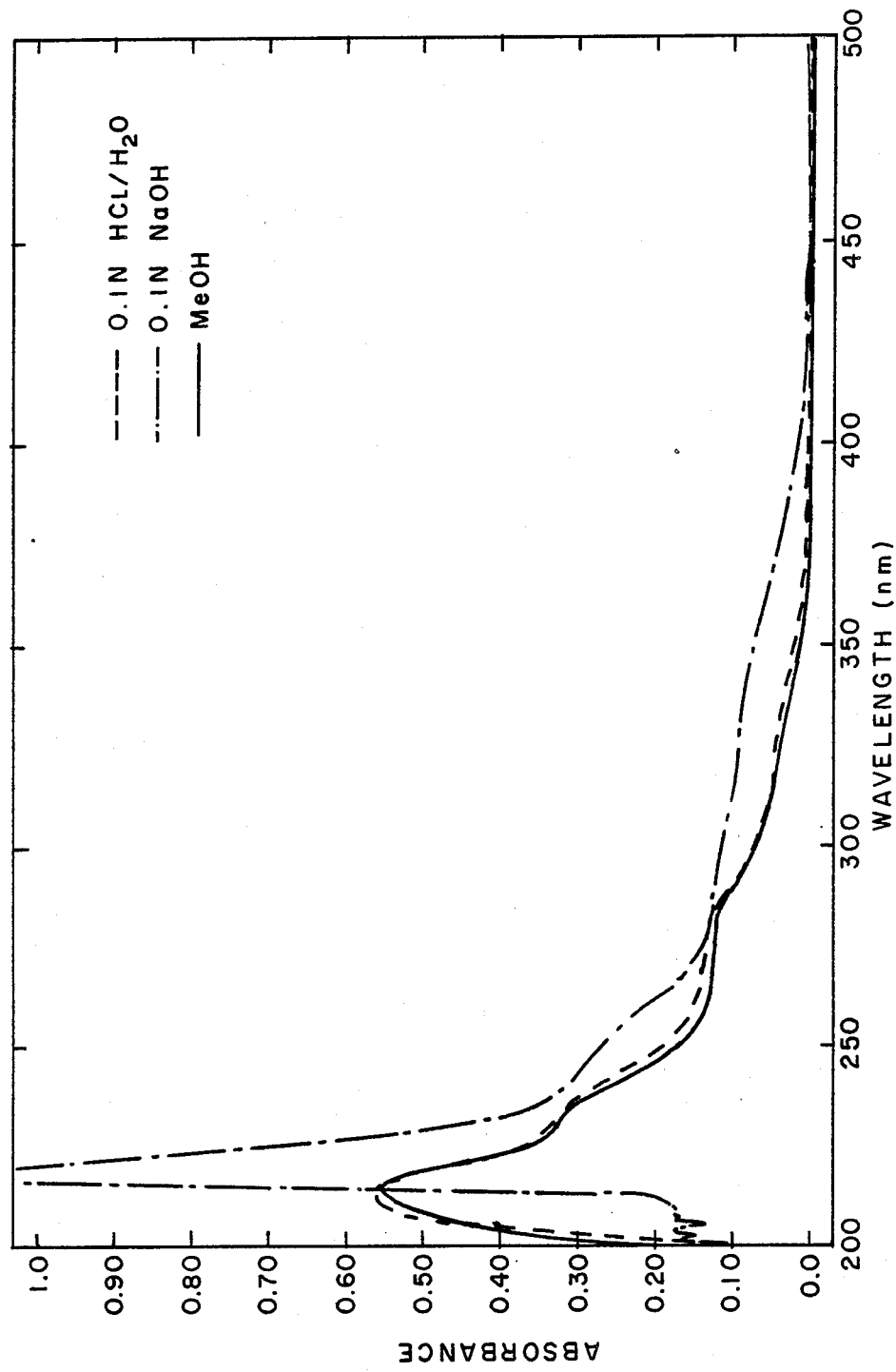

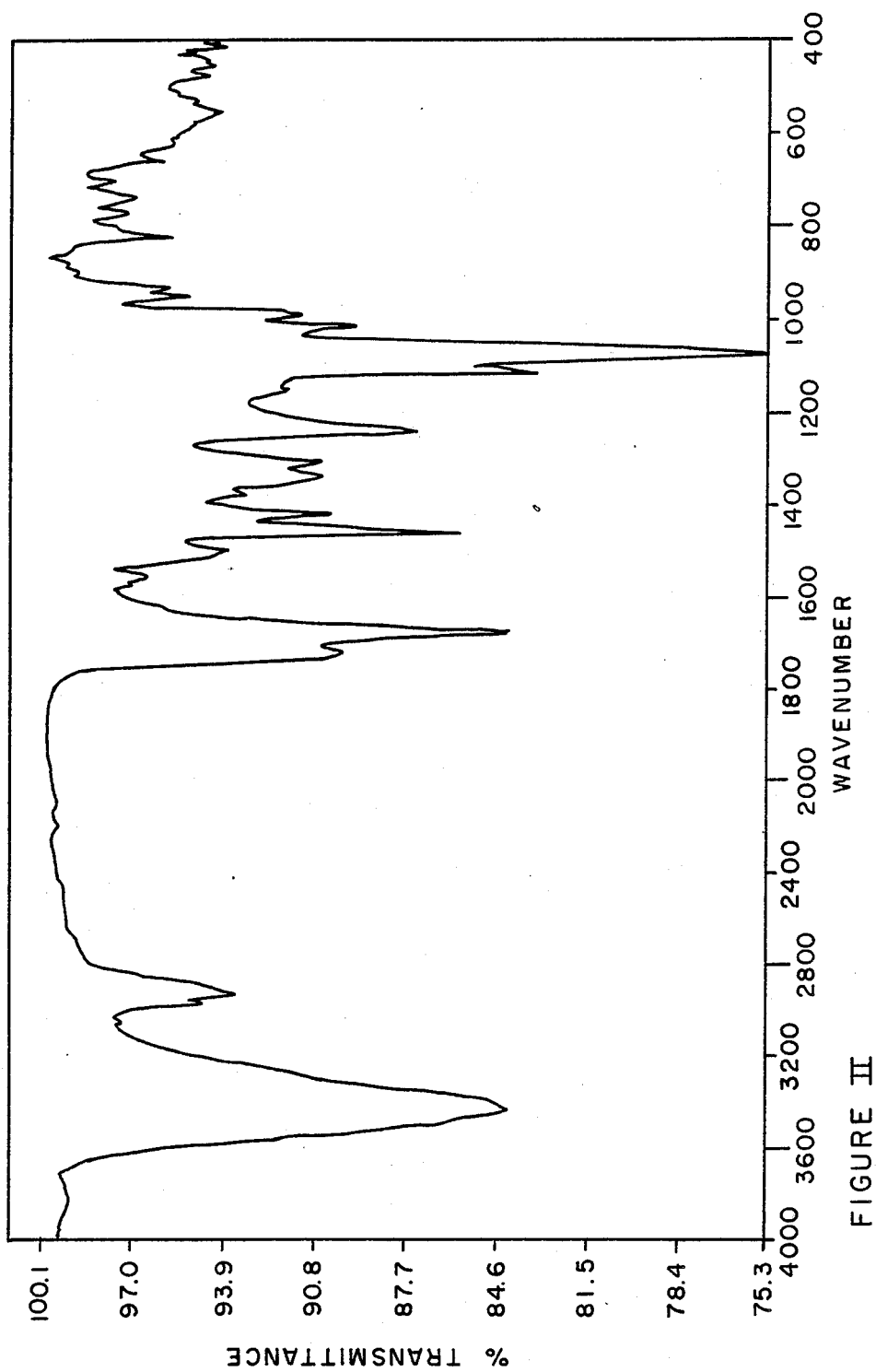
FIGURE II

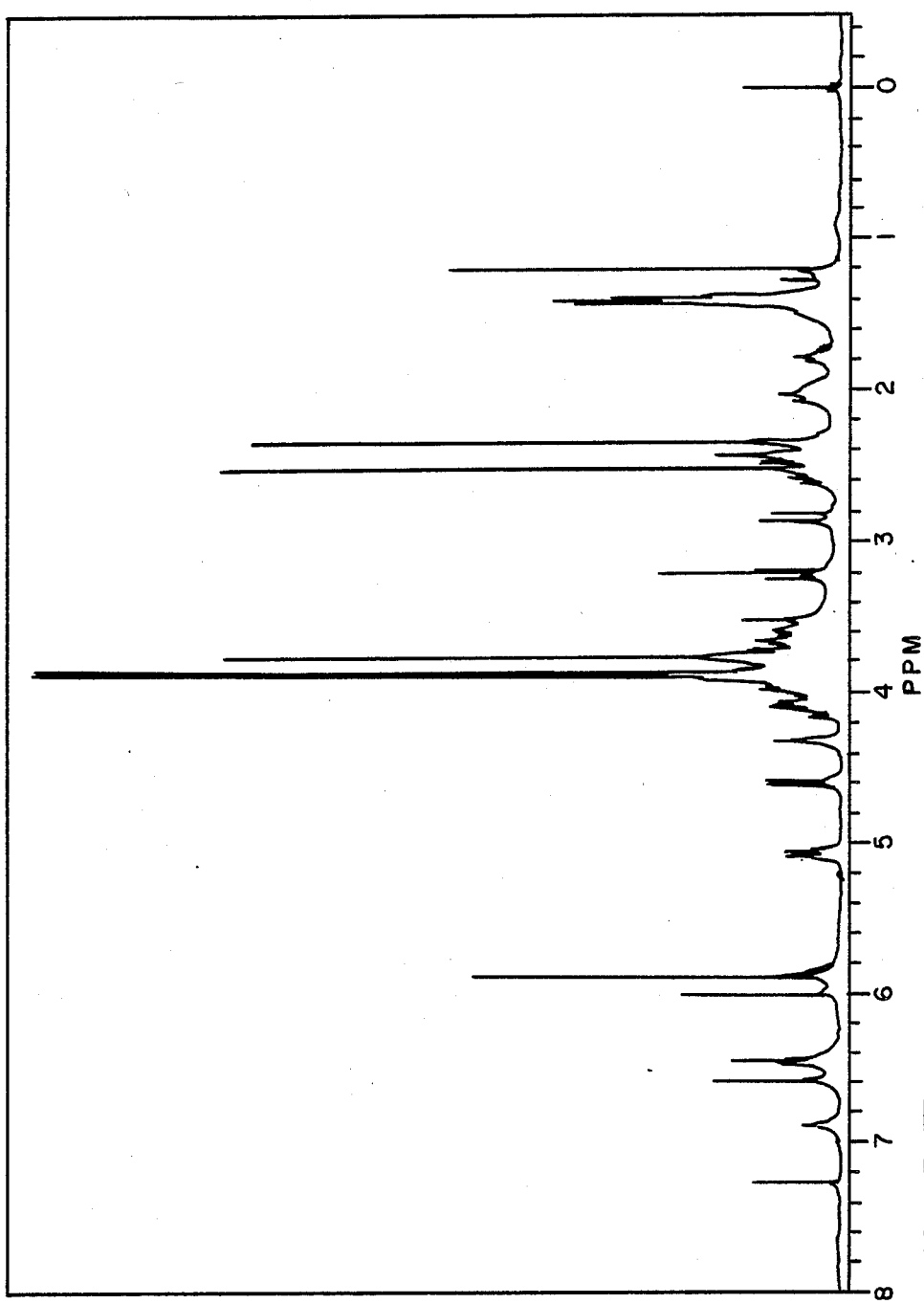
FIGURE III

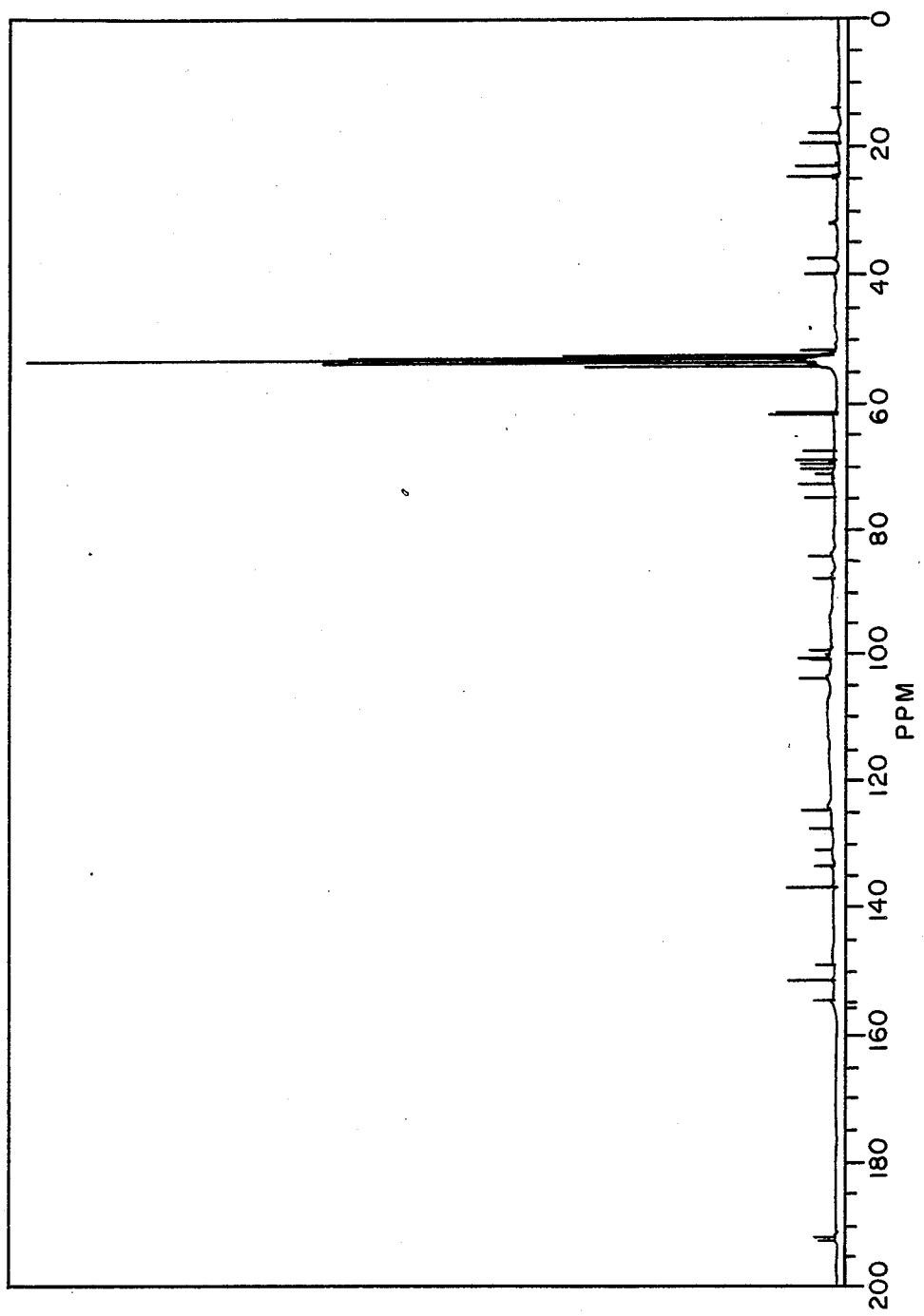
FIGURE IV

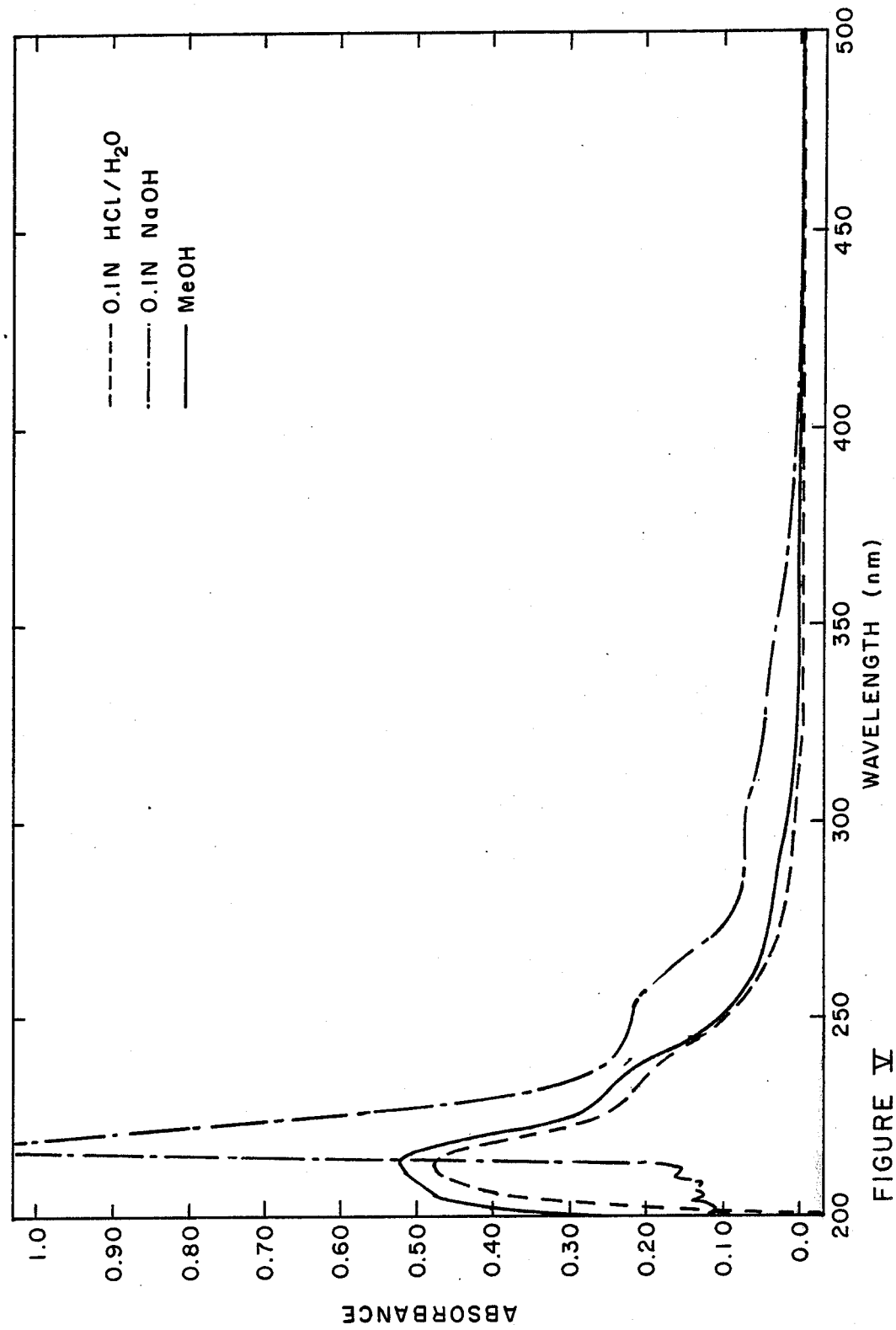

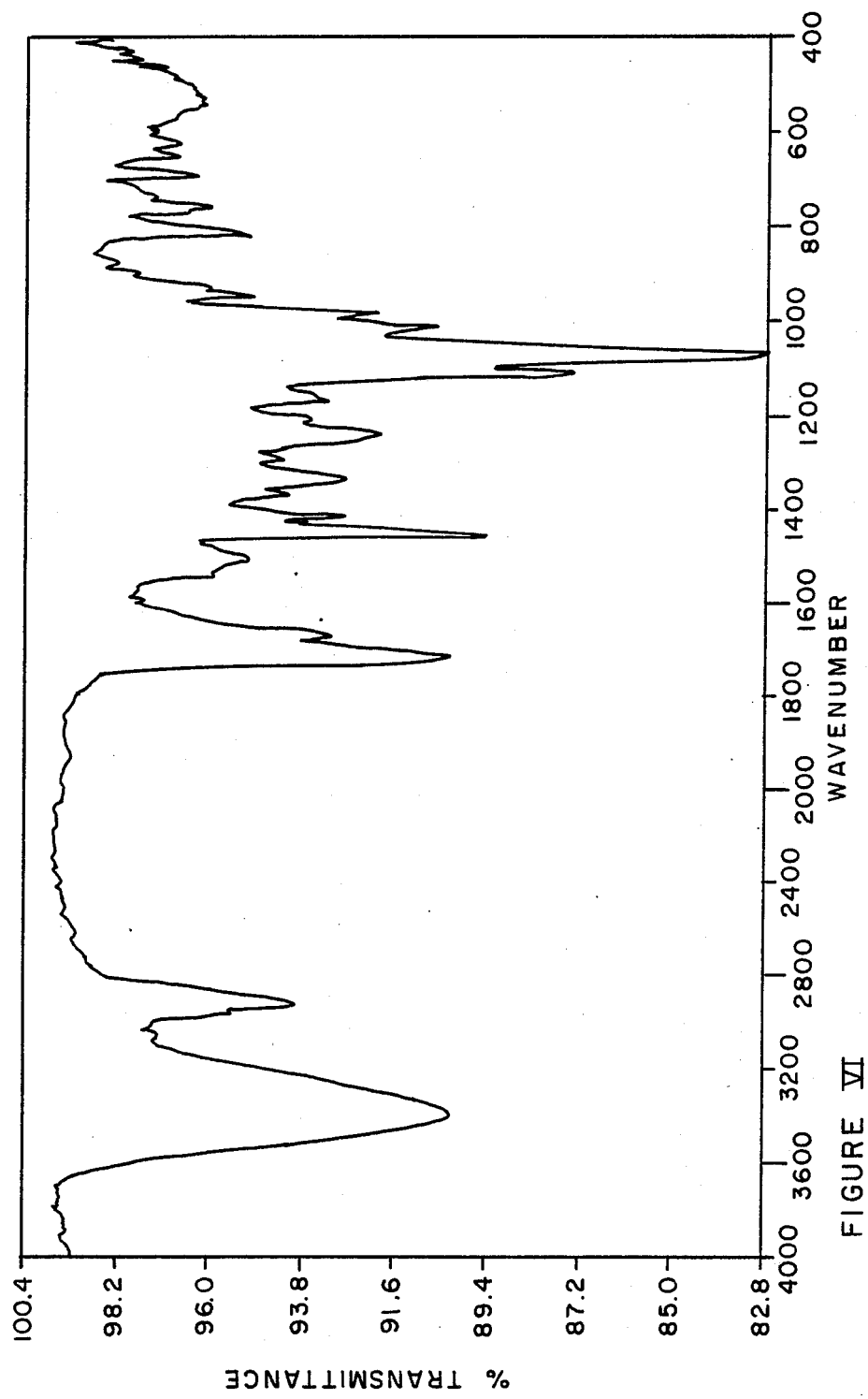

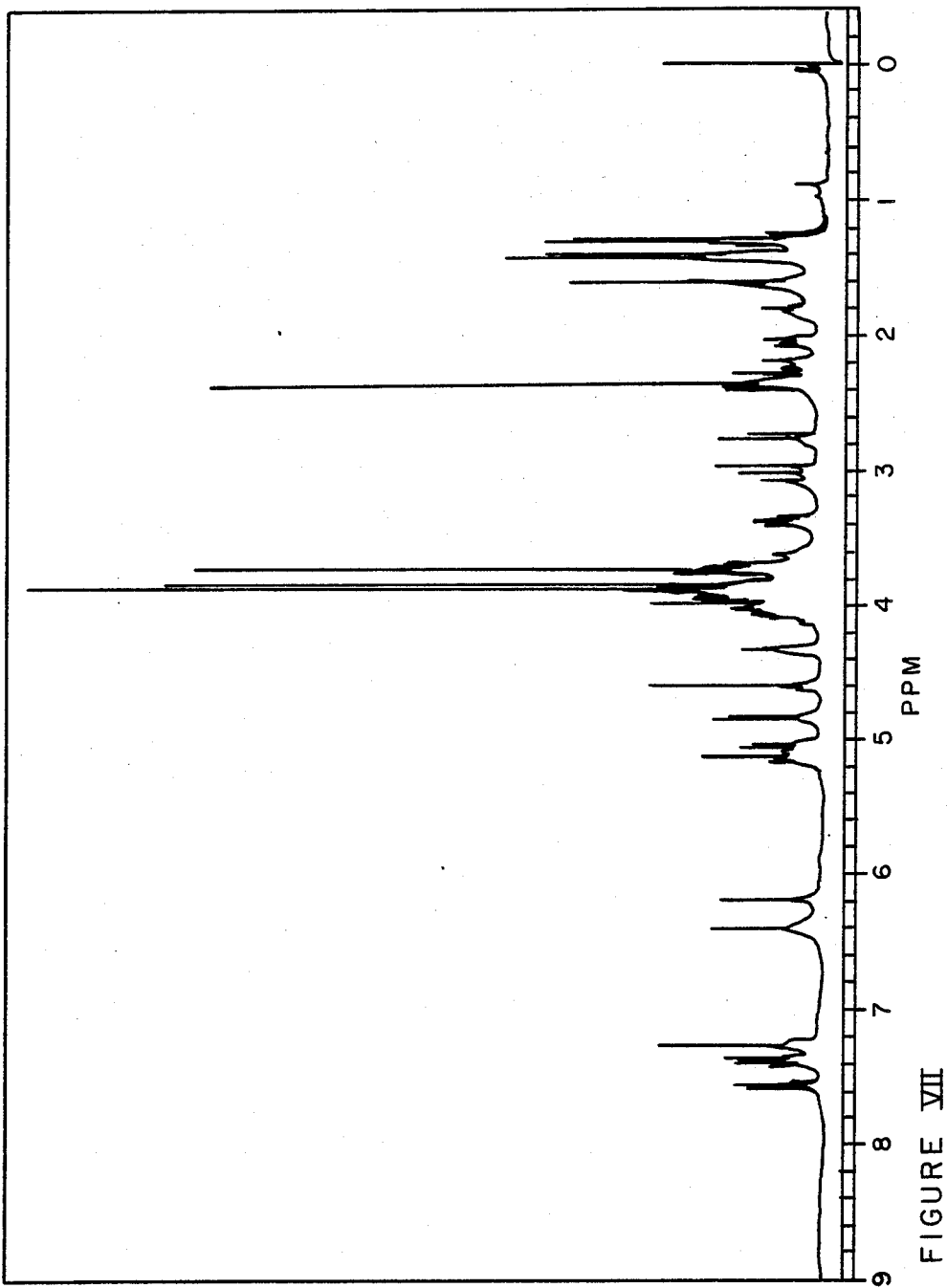
FIGURE VII

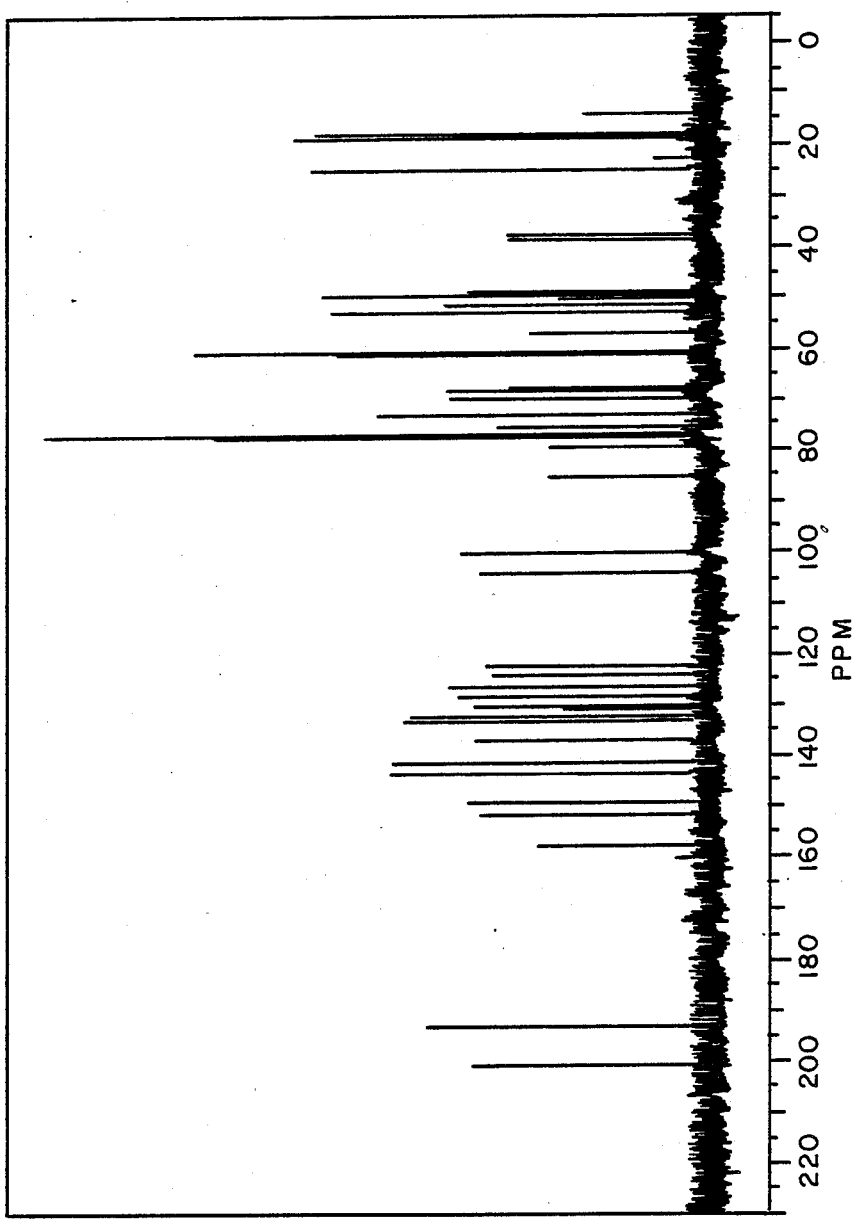
FIGURE VIII

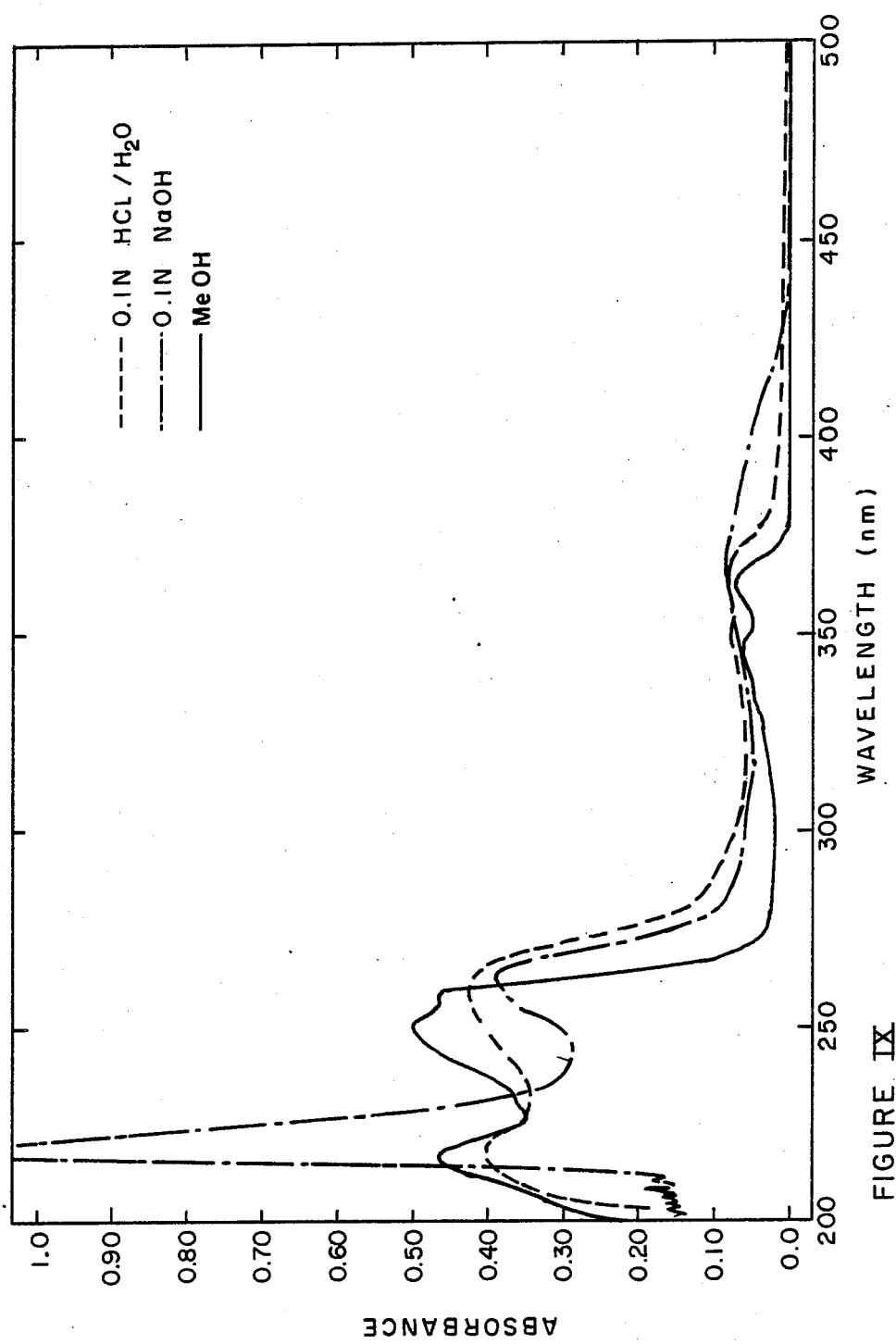

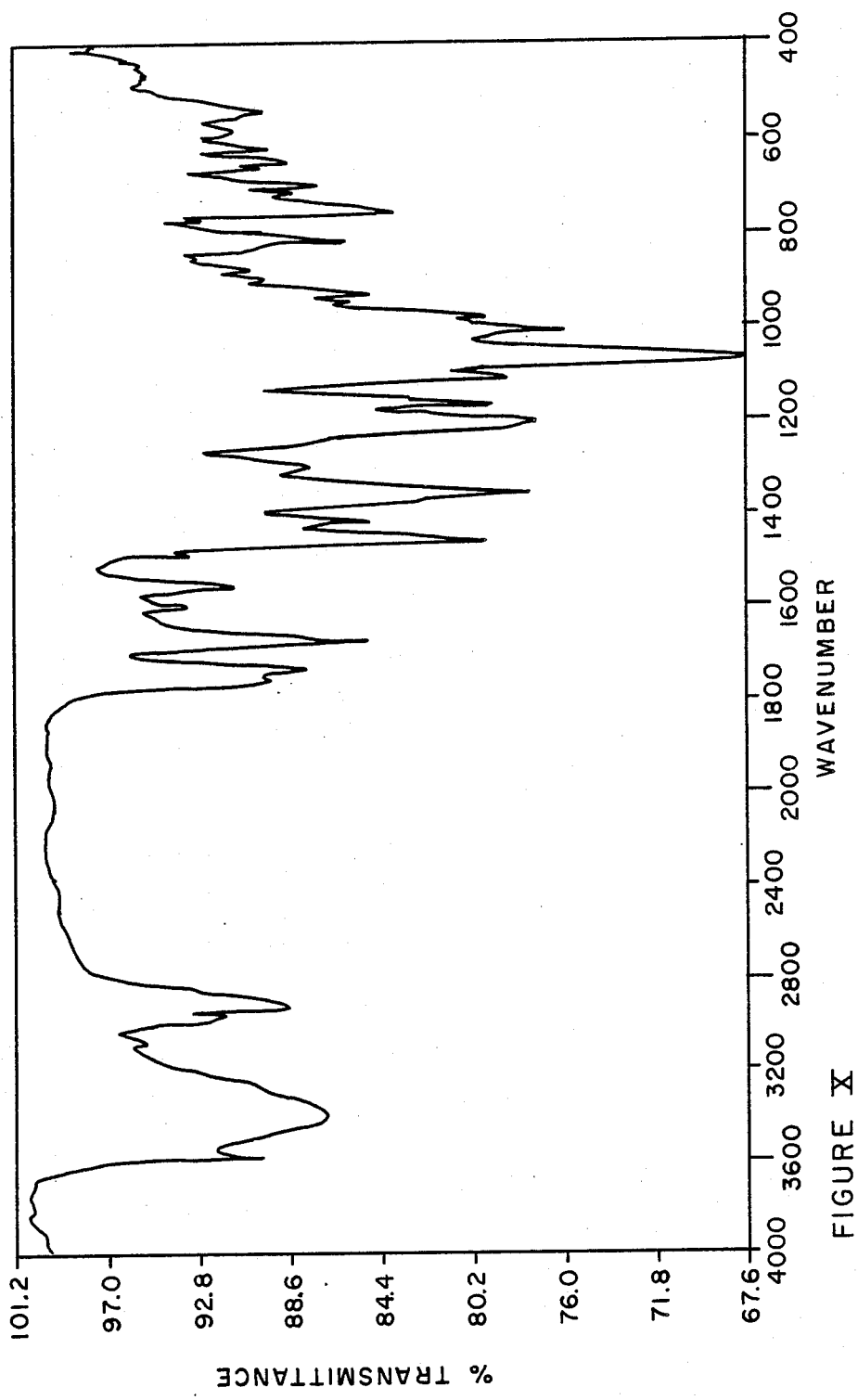
FIGURE X

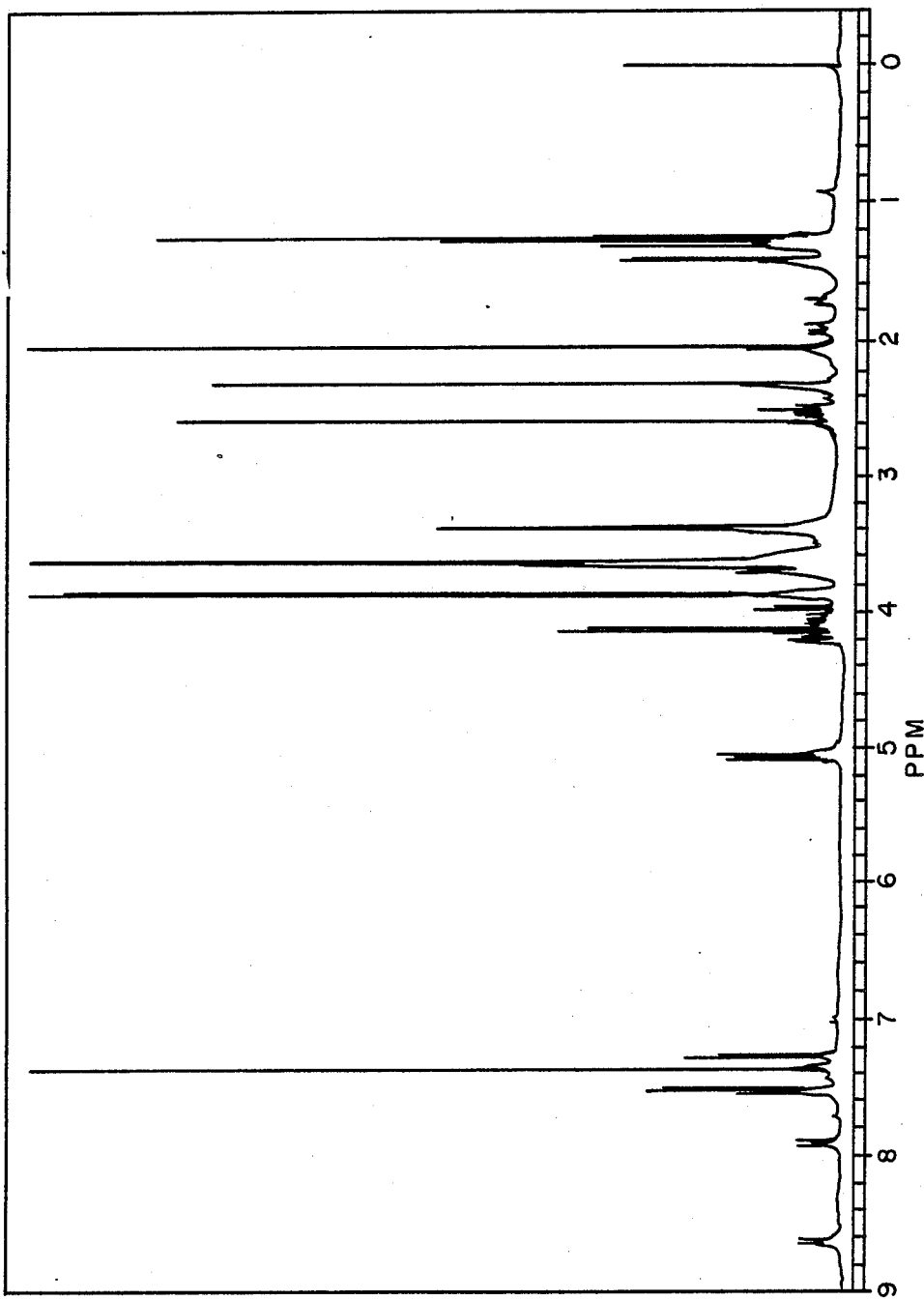
FIGURE XI

PSEUDOAGLYCONES OF LL-E33288 ANTIBIOTICS

BACKGROUND OF THE INVENTION

The LL-E33288 complex of antibiotics, having antibacterial and antitumor activity, are described and individually claimed in U.S. patent application, Ser. No. 07/009,321, filed concurrently herewith (Case 30,555), which application is a continuation-in-part of U.S. patent application, abandoned Ser. No. 787,066, filed Oct. 17, 1985, which application is a continuation-in-part of U.S. patent application, abandoned Ser. No. 672,031, filed Nov. 16, 1984 (Case 29,845).

The application, Ser. No. 787,066, filed Oct. 17, 1985, defines the individual components, namely LL-E33288$\alpha_1$-Br, LL-E3288$\alpha_1$-I, LL-E33288$\alpha_2$-Br, LL-E33288$\alpha_2$-I, LL-E33288$\alpha_3$-Br, LL-E33288$\alpha_3$-I, LL-E33288$\alpha_4$-Br, LL-33288$\beta_1$-Br, LL-E33288$\beta_1$-I, LL-E33288$\beta_2$-Br, LL-E33288$\beta_2$-I, LL-E33288$\gamma_1$-Br, LL-E33288$\gamma_1$-I, and LL-E33288$\delta_1$-I by specific physical and chemical characteristics, as well as detailing procedures for obtaining these components from the aerobic fermentation of a new *Micromonospora echinospora* ssp *calichensis*, NRRL 15839, and a derived mutant NRRL 15975.

All of the information contained in U.S. patent application, Ser. No. 07/009,321, filed concurrently herewith, is incorporated herein by reference. Pertinent information from the application is found in examples 4-6, below.

Certain other antibiotics are pertinent to this invention, namely: (1) Esperamicin BBM-1675, a novel class of potent antitumor antibiotics. I. Physico-chemical data and partial structure. M. Konishi, et al., J. Antibiotics, 38, 1605 (1985). A new antitumor antibiotic complex. M. Konishi, et al., U.S. Pat. No. 4,675,187 (1987). (2) New antitumor antibiotics, FR-900405 and FR-900406. I. Taxonomy of the producing strain. M. Iwami, et al., J. Antibiotics, 38, 835 (1985). New antitumor antibiotics FR-900405 and FR-900406. II. Production, isolation, characterization and antitumor activity. S. Kiyoto, et al., J. Antibiotics, 38, 840 (1985). (3) PD 114759 and PD 115028, novel antitumor antibiotics with phenomenal potency. I. Isolation and characterization. R. H. Bunge, et al., J. Antibiotics, 37, 1566 (1984). Biological and biochemical activities of the novel antitumor antibiotic PD 114759 and related derivatives. D. W. Fry, et al., Investigational New Drugs, 4, 3 (1986). (4) New antibiotic complex CL-1577A and CL-1577B produced by Streptomyces sp. ATCC 39363. European Patent application 0,132,082,A2. (5) CL-1577D and CL-1577E Antibiotic antitumor compounds, their production and use. U.S. Pat. No. 4,539,203. (6) CL-1724 Antibiotic compounds, their production and use. U.S. Pat. No. 4,554,162.

All of the information regarding BBM-1675, FR-900405, FR-900406, PD 114759, PD 115028, CL-1577A, CL-1577B, CL-1577D, CL-1577E and CL-1724 contained in the above citations is incorporated herein by reference.

DESCRIPTION OF THE INVENTION

This invention is concerned with degradation products of the LL-E33288 antibiotics as well as degradation products of the BBM-1675, FR-900405, FR-900406, PD 114759, PD 115028, CL-1577A, CL-1577B, CL-1577D, CL-1577E and CL-1724 antibiotics referred to in the background of the invention, all of which are derived in the same manner and all of which are described as pseudoaglycones.

These pseudoaglycones are all active as antibacterial and antitumor agents and are derived by the same general procedure. For simplicity the procedure and activity will be described with reference to the iodinated LL-E33288 antibiotics. However, it is apparent to one skilled in the art that similar procedure and activity can be described for other modification of the antibiotics, e.g., the brominated LL-E33288 antibiotics.

Proposed structures of some of the LL-E33288 antibiotics are disclosed below.

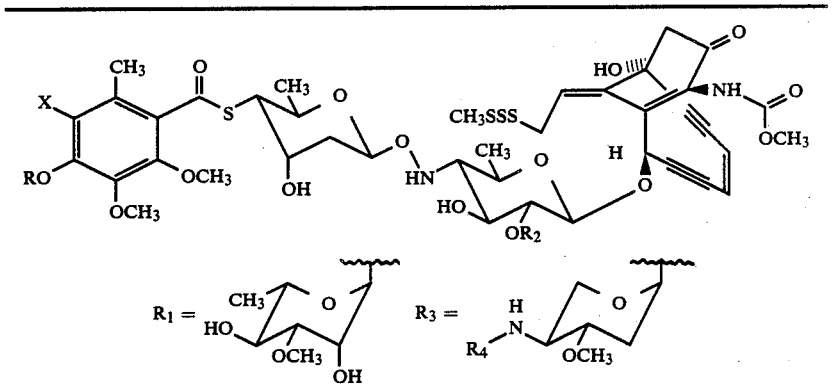

| E33288 | X | R | $R_2$ | $R_4$ |
|---|---|---|---|---|
| $\alpha_2^I$ | I | H | $R_3$ | $C_2H_5$ |
| $\alpha_3^I$ | I | $R_1$ | H | |
| $\beta_1^I$ | I | $R_1$ | $R_3$ | $(CH_3)_2CH$ |
| $\gamma_1^I$ | I | $R_1$ | $R_3$ | $C_2H_5$ |
| $\delta_1^I$ | I | $R_1$ | $R_3$ | $CH_3$ |
| $\beta_1^{Br}$ | Br | $R_1$ | $R_3$ | $(CH_3)_2CH$ |
| $\gamma_1^{Br}$ | Br | $R_1$ | $R_3$ | $C_2H_5$ |
| $\alpha_2^{Br}$ | Br | H | $R_3$ | $C_2H_5$ |
| $\alpha_3^{Br}$ | Br | $R_1$ | H | |

When a dilute methanolic solution of an iodinated LL-E33288 component such as LL-E33288$\gamma_1$-I is treated with a cation exchange resin such as Dowex ® 50W-X8(H+ form) the biologically active pseudoaglycone, having the following physico-chemical characteristics and proposed structure is obtained.

(a) Molecular weight: 1050, determined by FAB-MS;

(b) Molecular formula: $C_{40}H_{47}N_2O_{15}IS_4$, exact mass for M+Na was determined by high resolution FAB-MS to be 1073.0810 for $C_{40}H_{47}N_2O_{15}IS_4Na$;

(c) Ultraviolet absorption spectra: as shown in FIG. I (methanol; 0.1N HCl; 0.1N NAOH);

(d) Infrared absorption spectrum: as shown in FIG. II (KBr disc);

(e) Proton magnetic resonance spectrum: as shown in FIG. III (300 MHz, $CDCl_3$); and (f) Carbon-13 magnetic resonance spectrum: as shown in FIG. IV (75.43 MHz, $CDCl_3$, ppm from TMS) significant peaks as listed in Table I.

TABLE I

| Peak No. | PPM | Peak No. | PPM |
|---|---|---|---|
| 1 | 17.8 q | 21 | 84.4 s |
| 2 | 19.1 q | 22 | 87.5 s |
| 3 | 22.8 q | 23 | 98.7 s |
| 4 | 24.7 q | 24 | 99.7 d |
| 5 | 36.8 t | 25 | 100.4 s |
| 6 | 39.1 t | 26 | 103.5 d |
| 7 | 51.6 d | 27 | 124.1 d |
| 8 | 53.3 t | 28 | 124.2 d |
| 9 | 53.6 q | 29 | 126.8 s |
| 10 | 61.0 q | 30 | 127.5 d |
| 11 | 61.5 q | 31 | 130.6 s |
| 12 | 67.2 d | 32 | 133.2 s |
| 13 | 68.2 d | 33 | 136.3 s |
| 14 | 69.1 d | 34 | 136.4 s |
| 15 | 69.6 d | 35 | 140.7 s |
| 16 | 70.1 d | 36 | 148.8 s |
| 17 | 71.3 d | 37 | 150.9 s |
| 18 | 72.5 s | 38 | 154.3 s |
| 19 | 74.5 d | 39 | 191.8 s |
| 20 | 83.9 s | 40 | 192.0 s |

TABLE II

| Organism | | Minimal Inhibitory Concentration (mcg/ml) |
|---|---|---|
| Escherichia coli | CMC 84-11 | 2 |
| Escherichia coli | No. 311(MP) | 1 |
| Escherichia coli | ATCC 25922 | 1 |
| Klebsiella pneumoniae | CMC 84-5 | 2 |
| Klebsiella pneumoniae | AD(MP) | 0.5 |
| Enterobacter cloacae | CMC 84-4 | 4 |
| Enterobacter aerogenes | IO 83-44 | 4 |
| Serratia marcescens | CMC 83-27 | 1 |
| Serratia marcescens | F-35(MP) | 2 |
| Morganella morganii | IO 83-18 | 1 |
| Providencia stuartii | CMC 83-82 | 2 |
| Citrobacter diversus | K-82-24 | 2 |
| Citrobacter freundii | IO 83-13 | 1 |
| Acinetobacter sp. | CMC 83-89 | 2 |
| Acinetobacter sp | IO 83-49 | 4 |
| Pseudomonas aeruginosa | 12-4-4(Mp) | 2 |
| Pseudomonas aeruginosa | ATCC 27853 | 1 |
| Staphylococcus aureus | Smith(MP) | 0.03 |
| Staphylococcus aureus | SSC 82-21 | 0.12 |
| Staphylococcus aureus | ATCC 25923 | 0.25 |
| Staphylococcus aureus | SSC 82-20 | 0.25 |
| Staphylococcus aureus | SSC 82-23 | 0.12 |
| Staphylococcus aureus | SSC 82-24 | 0.03 |
| Staphylococcus aureus | SSC 82-54 | 0.12 |
| Staphylococcus epidermidis | CMC 83-133 | 0.008 |
| Staphylococcus epidermidis | ATCC 12228 | 0.015 |
| Streptococcus faecalis | ATCC 29212 | 0.12 |
| Streptococcus faecalis | CMC 83-53 | 0.5 |
| Streptococcus faecalis | IO 83-28 | 0.12 |

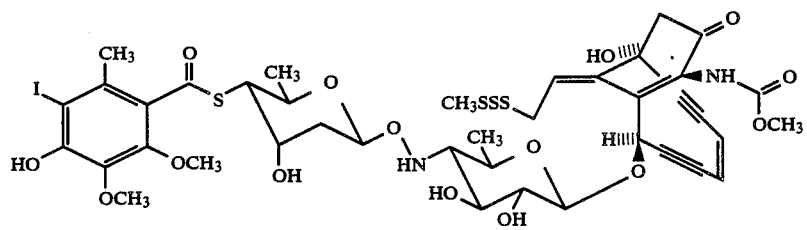

PSEUDOAGLYCONE OF LL-E33288

This pseudoaglycone is active as an antibacterial agent when tested by the standard agar dilution method. This activity was determined against a spectrum of gram-positive and gram-negative bacteria. Mueller-Hinton agar containing two-fold decreasing concentrations of pseudoaglycone was poured into petri plates. The agar surface was inoculated with 1 to $5 \times 10^6$ colony-forming units of bacteria by means of the Steers replicating device. The lowest concentration of the pseudoaglycone in mcg/ml that inhibited growth of a bacterial strain after about 18 hours of incubation at approximately 35° C. was recorded as the minimal inhibitory concentration (MIC) for that strain. The results appear in Table II.

This pseudoaglycone is also active as an antitumor agent as determined in the Biochemical Induction Assay (BIA), a bacterial assay system which specifically measures the ability of an agent to directly or indirectly initiate DNA damage. The indicator organism for this test is an E. coli-lambda lysogen, genetically constructed such that a DNA damaging event results in the expression of the gene for the enzyme β-galactosidase. This enzyme can be determined qualitatively or quantitatively by biochemical assay as an indication that DNA damage has occurred.

A modified version of the quantitative liquid BIA disclosed by Elespuru, R. and Yarmolinsky, M., Environmental Mutagenesis, 1, 65 (1979) was used to evaluate these compounds.

The antitumor activity of the pseudoaglycone of LL-E33288 was further demonstrated in the following test.

Lymphocytic leukemia P388 test

The animals used were BDF1 mice, all of one sex, weighing a minimum of 17 g and all within a 3 g weight range. There were 5 or 6 animals per test group. The tumor transplant was by intraperitoneal injection of 0.5 ml of dilute ascitic fluid containing $10^6$ cells of lymphocytic leukemia P388. The test compounds were administered intraperitoneally at the indicated doses at a volume of 0.5 ml in 0.2% Klucel in normal saline on days 1, 5 and 9, relative to tumor inoculation. The animals were weighed and survivors recorded on a regular basis for 30 days. The percent increase in life span was calculated from the ratio of survival time for treated/control mice. The results appear in Table III.

TABLE III

Lymphocytic Leukemia P388 Test

| Compound | Dose (mg/kg) | % Increased Life Span |
| --- | --- | --- |
| Pseudoaglycone of LL-E33288 | 200 | 164 |
|  | 160 | 178 |
|  | 80 | 157 |
|  | 40 | 154 |

TABLE III-continued

Lymphocytic Leukemia P388 Test

| Compound | Dose (mg/kg) | % Increased Life Span |
| --- | --- | --- |
|  | 20 | 154 |
|  | 10 | 146 |
|  | 5 | 125 |
|  | 2.5 | 127 |
|  | 1.2 | 114 |

When the pseudoaglycone of LL-E33288 is reacted with triphenylphosphine in a mixture of dichloromethane and methanol, the antibacterially inactive compound having the following physico-chemical characteristics and proposed structure is obtained.

(a) Molecular weight: 974, determined by FAB-MS;
(b) Molecular formula: $C_{39}H_{47}N_2O_{15}IS_4$, exact mass for M+Na was determined by high resolution FAB-MS to be 997.1370 for $C_{39}H_{47}N_2O_{15}IS_2Na$;
(c) Ultraviolet absorption spectra: as shown in FIG. V (methanol; 0.1N HCl; 0.1N NaOH);
(d) Infrared absorption spectrum: as shown in FIG. VI (KBr disc);
(e) Proton magnetic resonance spectrum: as shown in FIG. VII (300 MHz, $CDCl_3$);
(f) Carbon-13 magnetic resonance spectrum: as shown in FIG. VIII (75.43 MHz, $CDCl_3$, ppm from TMS) significant peaks as listed in Table IV.

TABLE IV

| Peak No. | PPM | Peak No. | PPM |
| --- | --- | --- | --- |
| 1 | 17.8 q | 21 | 80.1 d |
| 2 | 19.1 q | 22 | 84.3 d |
| 4 | 24.7 q | 23 | 99.7 d |
| 5 | 36.7 t | 24 | 104.8 d |
| 6 | 38.5 t | 25 | 122.5 d |
| 7 | 51.9 q | 26 | 124.1 d |
| 8 | 52.8 q | 27 | 126.9 d |
| 9 | 56.6 t | 28 | 128.8 d |
| 10 | 61.1 q | 29 | 130.7 d |
| 11 | 61.5 q | 30 | 131.3 d |
| 12 | 67.2 d | 31 | 132.3 s |
| 13 | 68.3 d | 32 | 133.2 s |
| 14 | 69.0 d | 33 | 136.5 s |
| 15 | 69.2 d | 34 | 140.3 s |
| 16 | 69.2 d | 35 | 143.3 s |
| 17 | 70.1 d | 36 | 148.9 s |
| 18 | 73.0 s | 37 | 150.9 s |
| 19 | 73.5 s | 38 | 157.1 s |
| 20 | 75.2 d | 39 | 191.8 s |
|  |  | 40 | 199.8 s |

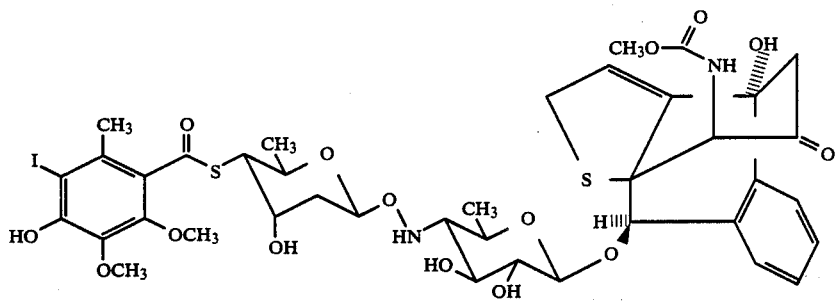

When the product derived from reacting the pseudoaglycone of LL-E33288 with triphenylphosphine in a mixture of dichloromethane and methanol is reacted first with a methanolic solution of potassium carbonate and then excess acetic anhydride, the compound having the following physico-chemical characteristics and structure is obtained. This compound is crystalline and its chemical structure was determined by X-ray crystallography.

(a) Ultraviolet absorption spectra: as shown in FIG. IX (methanol; 0.1N HCl; 0.1N NaOH);

(b) Infrared absorption spectrum: as shown in FIG. X (KBr disc);

(c) Proton magnetic resonance spectrum: as shown in FIG. XI (300 MHz, CDCl$_3$, containing trace ethyl acetate);

(d) Molecular formula: C$_{36}$H$_{40}$NO$_{13}$IS$_2$, calculated from the chemical structure.

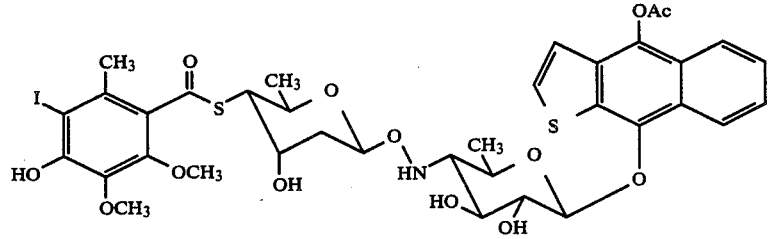

The invention will be further described in conjunction with the following examples.

EXAMPLE 1

Preparation of the Pseudoaglycone of LL-E33288

A methanolic solution of partially purified LL-E33288$\gamma_1$-I (prepared as described in Example 6. 408 mg, 65% pure, in 5 ml) was passed slowly through a column (1.5×30 cm) packed with Dowex ® 50W-X8 (50–100 mesh, hydrogen form) prewashed with dichloromethane and methanol and equilibrated with methanol. The column effluent was monitored by TLC (Whatman LHP-KP Linear-K high performance silica gel precoated glass plates, ethyl acetate saturated with 0.1M phosphate buffered at pH 7 elution, detected by UV$_{254\ nm}$ quenching and charring after spraying with a solution of #5 cupric acetate in 8% aqueous phosphoric acid) and was recycled back onto the column until no $\gamma_1$-I was detected. The column was eluted with 4 liters of methanol overnight, the eluate was collected and concentrated in vacuo to dryness. The light yellow residue was triturated with t-butyl methyl ether and the insolubles were redissolved in ethyl acetate and precipitated by addition of hexane to yield 121 mg of 82% pure pseudoaglycone of LL-E33288.

The 82% pure pseudoaglycone of LL-E33288 was further purified by chromatography on a Bio-Sil ® A (20–44$\mu$) column (0.9×25 cm) eluting with dichloromethane: methanol (95:5) to yield 73 mg of analytically pure pseudoaglycone of LL-33288.

EXAMPLE 2

Preparation of triphenylphosphine reaction product of the pseudoaglycone of LL-33288

A 279 mg sample of 80% pure pseudoaglycone of LL-E33288 was dissolved in a mixture of 40 ml of dichloromethane and 20 ml of methanol. A 140 mg portion of triphenylphosphine was added and the reaction mixture was stirred under argon for 3 hours. The mixture was concentrated in vacuo to dryness. The residue was redissolved in ethyl acetate and precipitated by the addition of hexane. The precipitate was chromatographed on a Woelm silica (32–63$\mu$) column, eluting with dichloromethane: methanol (95:5). Fractions containing the desired material [Rf 0.23, Whatman LHP-KF Linear-K high performance silica gel precoated glass plates, dichloromethane: methanol (94:6) elution] were pooled and worked up by concentration and precipitation to yield 67 mg of 90% pure triphenylphosphine reaction product of the pseudoaglycone of LL-E33288.

The 90% pure triphenylphosphine reaction product of the pseudoaglycone of LL-33288 was further purified by preparative TLC on two Analtech, 20×20 cm, 2000$\mu$ layer, silica gel GF precoated plates, eluting with ethyl acetate saturated with 0.1M phosphate buffer at pH 7. The major UV$_{254\ nm}$ quenching band (Rf 0.4) was worked up to yield 49 mg of analytically pure triphenylphosphine reaction product of the pseudoaglycone of LL-E33288.

EXAMPLE 3

Preparation of the reaction product of the product, derived from reacting the pseudoaglycone of LL-E33288 with triphenylphosphine, with methanolic potassium carbonate and then excess acetic anhydride A 46 mg sample of 90% triphenylphosphine reaction product of the pseudoaglycone of LL-E33288 was dissolved in 4 ml of methanol and 4 ml of a saturated methanolic solution of potassium carbonate was added. The reaction mixture was allowed to remain at room temperature for 5 minutes, then was treated with 400 $\mu$l of acetic anhydride and allowed to remain at 4° C. for 2 hours. After neutralization with methanolic potassium carbonate, the reaction mixture was concentrated in vacuo to dryness. The residue was chromatographed on two Analtech, 20×20 cm, 2000$\mu$ layer, silica gel GF precoated plates, eluting with dichloromethane: methanol (94:6). The two major UV$_{254\ nm}$ quenching, UV$_{366\ nm}$ blue fluorescent bands, chromatographing close to each other, were worked up together and the mixture was rechromatographed on four Analtech, 20×20 cm, 1000$\mu$ layer, silica gel GF precoated plates, eluting with the same solvent system to yield 7.5 mg of crystalline compound, which was recrystallized from a mixture of methanol and chloroform to give crystals suitable for x-ray crystallography.

Preparation of the iodinated LL-E 33288 complex A three stage inoculum was prepared using a culture of *Micromonospora echinospora* ssp. *calichensis* NRRL018149. The inoculum media were of the following formulation:

| Ingredient | per/liter |
| --- | --- |
| Calcium carbonate | 4 g |
| Hodag ® FD82 | 1 ml |
| Dextrin | 24 g |
| Glucose | 5 g |
| Yeast extract | 5 g |
| Tryptone | 5 g |

| Ingredient | per/liter |
| --- | --- |
| Beef extract | 3 g |
| water qs | |

A 150 liter portion of the stage III inoculum was used to inoculate 1500 liter fermentation medium of the following composition:

| Ingredient | per/liter |
| --- | --- |
| Sucrose | 20.0 g |
| Ferrous sulfate heptahydrate | 0.1 g |
| Magnesium sulfate heptahydrate | 0.2 g |
| Peptone | 5.0 g |
| Molasses | 5.0 g |
| Potassium iodide | 0.5 g |
| Calcium carbonate | 5.0 g |
| Hodag ® FD 82 | 5.0 ml |
| water qs | |

The fermentation was carried out at 30° C., with a sterile air flow of 0.75 VVM, a back pressure of 8 psig and agitation at 120 rpm for 5–6 days at which time the mash was harvested.

The harvested mash was extracted with an equal volume of ethyl acetate. The organic phase, containing the iodinated LL-E33288 complex, was concentrated to a syrup and was poured into 7–8 times its volume of rapidly stirred hexane. The hexane insoluble gum, containing the iodinated LL-E33288 complex, was redissolved in ethyl acetate and was precipitated by addition of ether and hexane. The precipitate was collected to yield 53 g of iodinated LL-E33288 complex.

EXAMPLE 5

Preparation of the brominated LL-E33288 complex

The brominated LL-E33288 complex was prepared by exactly the same method as described in Example 4 for the preparation of the iodinated LL-E33288 complex with the exception that potassium bromide instead of potassium iodide was used in the fermentation medium.

EXAMPLE 6

Preparation of LL-E33288$_{\gamma 1}$-I from the iodinated LL-E33288 complex.

The iodinated LL-E33288 complex prepared as described in Example 4 was chromatographed on Sepralyte ® C-18 column, eluting with acetonitrile: 0.2M aqueous ammonium acetate (45:55). Each fraction was analyzed by TLC (EM silica gel 60F$_{254}$ pre-coated aluminum sheets, 3% isopropanol in ethyl acetate saturated with 0.1M KH$_2$PO$_4$ elution, detected with UV$_{254\ nm}$ quenching and bioautography via and biochemical induction assay, Rf 0.28 for LL-E33288$_{\gamma 1}$-I) and those containing LL-E33288$_{\gamma 1}$-I were pooled and worked up to give partially purified LL-E33288$_{\gamma 1}$-I.

EXAMPLE 7

Preparation of the iodinated LL-E33288 pseudoaglycone from the iodinated LL-E33288 complex.

A methanolic solution of the iodinated LL-E33288 complex as prepared in Example 4 is passed slowly through a Dowex ® 50W-X8 (hydrogen form) column which is prewashed with dichloromethane and methanol and equilibrated with methanol. The effluent of the column is recycled back onto the column until no LL-E33288 antibiotic is detected. The column is then eluted with 75–100 bed volumes of methanol to produce the iodinated LL-E33288 pseudoaglycone. The column eluate containing the iodinated LL-E33288 pseudoaglycone is concentrated to dryness and the residue is triturated with t-butyl methyl ether. The t-butyl methyl ether insolubles are redissolved in ethyl acetate and the iodinated LL-E33288 pseudoaglycone is precipitated by addition of hexane. The iodinated LL-E33288 pseudoaglycone thus obtained is further purified by column chromatography on Bio-Sil ® A.

EXAMPLE 8

Preparation of the brominated LL-E33288 pseudoaglycone from the brominated LL-E33288 complex The brominated LL-E33288 pseudoaglycone is prepared from the brominated LL-E33288 complex following essentially the same procedure as described in Example 7 for the preparation of the iodinated LL-E33288 pseudoaglycone from the iodinated LL-E33288 complex.

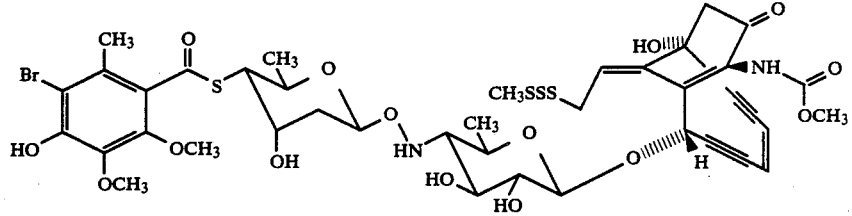

EXAMPLE 9

Preparation of the pseudoaglycone of BBM-1675 from the BBM-1675 complex

The pseudoaglycone of BBM-1675 is prepared from the BBM-1675 complex following essentially the same procedure as described in Example 7 for the preparation of the iodinated LL-E33288 pseudoaglycone from the iodinated LL-E33288 complex.

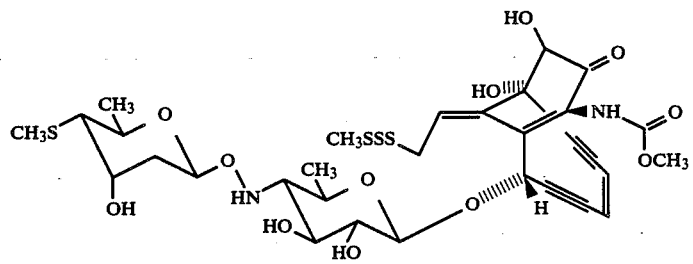

I claim:
1. A process for preparing the pseudoaglycone of an antibiotic of the LL-E33288 complex or the BBM-1675 complex which comprises
absorbing the antibiotic onto a column packed with a cation exchange resin in the hydrogen form,
eluting the column with large quantities of methanol to produce the pseudoaglycone of the antibiotic,
removing the resulting pseudoaglycone product from the acidic environment and
isolating the pseudoaglycone by chromatographic purification.

2. The iodinated pseudoaglycone of LL-E33288, when prepared by the process of claim 1, having the following identifying characteristics:
(a) a molecular weight of 1050 (FAB-MS);
(b) a molecular formula: $C_{40}H_{47}N_2O_{15}IS_4$;
(c) ultraviolet absorption spectra as shown in FIG. I;
(d) an infrared absorption spectrum as shown in FIG. II;
(e) a proton magnetic resonance spectrum as shown in FIG. III;
(f) a carbon-13 magnetic resonance spectrum as shown in FIG. IV, with significant peaks as follows:

| Peak No. | PPM | Peak No. | PPM |
|---|---|---|---|
| 1 | 17.8 q | 21 | 84.4 s |
| 2 | 19.1 q | 22 | 87.5 s |
| 3 | 22.8 q | 23 | 98.7 s |
| 4 | 24.7 q | 24 | 99.7 d |
| 5 | 36.8 t | 25 | 100.4 s |
| 6 | 39.1 t | 26 | 103.5 d |
| 7 | 51.6 d | 27 | 124.1 d |
| 8 | 53.3 t | 28 | 124.2 d |
| 9 | 53.6 q | 29 | 126.8 s |
| 10 | 61.0 q | 30 | 127.5 d |
| 11 | 61.5 q | 31 | 130.6 s |
| 12 | 67.2 d | 32 | 133.2 s |
| 13 | 68.2 d | 33 | 136.3 s |
| 14 | 69.1 d | 34 | 136.4 s |
| 15 | 69.6 d | 35 | 140.7 s |
| 16 | 70.1 d | 36 | 148.8 s |
| 17 | 71.3 d | 37 | 150.9 s |
| 18 | 72.5 s | 38 | 154.3 s |
| 19 | 74.5 d | 39 | 191.8 s |
| 20 | 83.9 s | 40 | 192.0 s |

(g) and which, when reacted with triphenylphosphine in a mixture of dichloromethane and methanol produces a compound having the following physico-chemical characteristics:
(a') a molecular weight of 974 (FAB-MS);
(b') a molecular formula: $C_{39}H_{47}N_2O_{15}IS_4$;
(c') ultraviolet absorption spectra as shown in FIG. V;
(d') an infrared absorption spectrum as shown in FIG. VI;
(e') a proton magnetic resonance spectrum as shown in FIG. VII;
(f') a carbon-13 magnetic resonance spectrum as shown in FIG. VIII, with significant peaks as follows:

| Peak No. | PPM | Peak No. | PPM |
|---|---|---|---|
| 1 | 17.8 q | 21 | 80.1 d |
| 2 | 19.1 q | 22 | 84.3 d |
| 4 | 24.7 q | 23 | 99.7 d |
| 5 | 36.7 t | 24 | 104.8 d |
| 6 | 38.5 t | 25 | 122.5 d |
| 7 | 51.9 q | 26 | 124.1 d |
| 8 | 52.8 q | 27 | 126.9 d |
| 9 | 56.6 t | 28 | 128.8 d |
| 10 | 61.1 q | 29 | 130.7 d |
| 11 | 61.5 q | 30 | 131.3 d |
| 12 | 67.2 d | 31 | 132.3 s |
| 13 | 68.3 d | 32 | 133.2 s |
| 14 | 69.0 d | 33 | 136.5 s |
| 15 | 69.2 d | 34 | 140.3 s |
| 16 | 69.2 d | 35 | 143.3 s |
| 17 | 70.1 d | 36 | 148.9 s |
| 18 | 73.0 s | 37 | 150.9 s |
| 19 | 73.5 s | 38 | 157.1 s |
| 20 | 75.2 d | 39 | 191.8 s |
|  |  | 40 | 199.8 s |

(h) and which, when the product described in (g) is reacted with a methanolic solution of potassium carbonate followed by an excess of acetic anhydride produces a compound having the following physicochemical characteristics:
(a") ultraviolet absorption spectra as shown in FIG. IX;
(b") an infrared absorption spectrum as shown in FIG. X;
(c") a proton magnetic resonance spectrum as shown in FIG. XI;
(d") a molecular formula: $C_{36}H_{40}NO_{13}IS_2$;
(e") and a chemical structure determined by x-ray crystallography to be as shown:

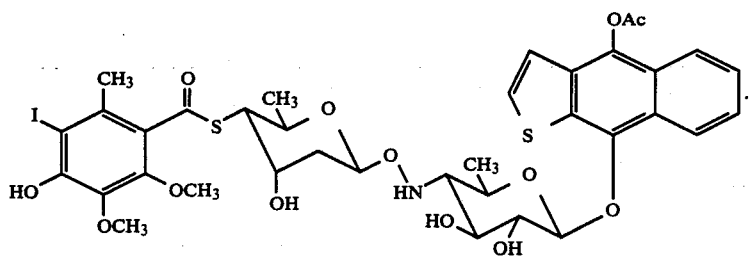
3. A compound pseudoaglycone of BBM-1675, when prepared by the process of claim 1.
4. A brominated pseudoaglycone of LL-E33288.